(12) United States Patent
Tam et al.

(10) Patent No.: US 6,459,756 B1
(45) Date of Patent: Oct. 1, 2002

(54) SYSTEM AND METHOD FOR PROVIDING NORMALIZATION CORRECTION FOR IMAGE RECONSTRUCTION IN A REDUCED PITCH SPIRAL SCAN CONE BEAM COMPUTED TOMOGRAPHY IMAGING SYSTEM

(75) Inventors: Kwok Tam, Edison, NJ (US); Günter Lauritsch, Erlangen (DE); Herbert Bruder, Höchstadt (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 10/015,797

(22) Filed: Oct. 30, 2001

(51) Int. Cl.$^7$ ................................................ A61B 6/03
(52) U.S. Cl. ........................................ 378/15; 378/901
(58) Field of Search ........................... 378/4, 8, 19, 901

(56) References Cited

U.S. PATENT DOCUMENTS

| | | |
|---|---|---|
| 5,390,112 A | 2/1995 | Tam |
| 5,463,666 A | 10/1995 | Eberhard et al. ............... 378/4 |
| 5,504,792 A | 4/1996 | Tam ............................ 378/15 |
| 6,292,525 B1 | 9/2001 | Tam ............................. 378/4 |
| 6,330,298 B1 * | 12/2001 | Tam ............................ 378/15 |

FOREIGN PATENT DOCUMENTS

EP      0981995 A2    3/2000

* cited by examiner

Primary Examiner—David V. Bruce
(74) Attorney, Agent, or Firm—Donald B. Paschburg (57) ABSTRACT

A system and method for 3D image reconstruction in a spiral scan cone beam computed tomography (CT) imaging system that allows the pitch of spiral scan projection to be reduced by a factor of 1/n (where n=3, 5, 7, 9, etc), thereby increasing the x-ray dosage to obtain a higher S/N (signal-to-noise) ratio, while achieving efficient use of a fixed-size detector. In addition, an image reconstruction protocol computes a correction factor for integration planes that intersect the reduced-pitch spiral path (which surrounds a ROI) at only M<n locations within an angular range that is determined, e.g., for M=1 planes, based on mask boundaries applied to the cone beam data. Despite the reduced pitch, the M<n integration planes do not provide increased flux (in contrast to other integration planes that intersect the object and scan path in M≥n locations).

16 Claims, 9 Drawing Sheets

Common tangents to the 2 mask boundaries

SYSTEM AND METHOD FOR PROVIDING NORMALIZATION CORRECTION FOR IMAGE RECONSTRUCTION IN A REDUCED PITCH SPIRAL SCAN CONE BEAM COMPUTED TOMOGRAPHY IMAGING SYSTEM

BACKGROUND

1. Technical Field

The present invention relates generally to a system and method for 3-dimensional (3D) image reconstruction in a spiral scan cone beam computed tomography (CT) imaging system and, more specifically, to a spiral scan cone beam CT system and method that computes a normalization correction for image reconstruction when a reduced pitch spiral scan is used to acquire cone beam projection data using a fixed size detector.

2. Description of Related Art

A system employing cone beam geometry has been developed for three-dimensional (3D) computed tomography (CT) imaging that comprises a cone beam x-ray source and a 2D area detector. A 2D area detector used for 3D imaging generally has detector elements arranged in a 2D array of rows and columns. An object to be imaged is scanned, preferably over a 360 degree angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

U.S. Pat. No. 5,390,112 entitled "THREE-DIMENSIONAL COMPUTERIZED TOMOGRAPHY SCANNING METHOD AND SYSTEM FOR IMAGING LARGE OBJECTS WITH SMALLER AREA DETECTORS", issued on Feb. 14, 1995 to Kwok Tam, and U.S. Pat. No. 5,463,666 entitled "HELICAL AND CIRCLE SCAN REGION OF INTEREST COMPUTERIZED TOMOGRAPHY", which issued on Oct. 31, 1995, both of which are incorporated herein by reference, describe a spiral scan cone beam CT system in which an x-ray source following a spiral scan path is used to image a relatively long object, wherein the x-ray detector is much shorter than the object. The only height requirement for the detector is that it be longer than the distance between adjacent turns in the spiral scan of the x-ray source.

Figure 2:
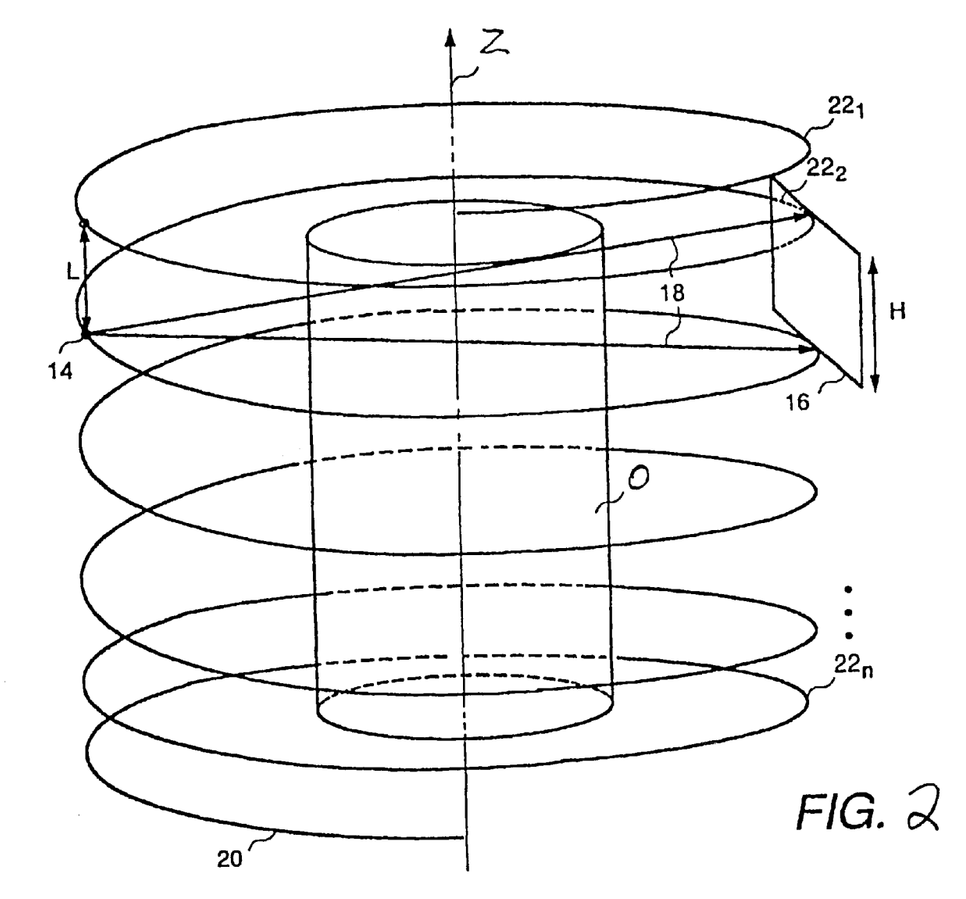
FIG. 2 is an exemplary diagram of a source scanning trajectory having a helical path and comprising a plurality of stages for scanning an object.

More specifically, FIG. 2 is an exemplary diagram of a scanning trajectory 20. Specifically, the source scanning trajectory 20 comprises a helical (spiral) path located on the surface of a predetermined geometric surface (such as a cylinder) radially centered on axis Z. The helical path 20 defines a plurality of stages $21_1$, $22_2$, . . . $22_n$ that are mutually spaced and surrounding an object O (or a region of interest (ROI) portion of an object) under examination such that each plane passing through the object O intersects the scanning trajectory 20 in at least one point. The term stage refers to each of the turns or revolutions formed by the helical path about axis 12, for example.

As the cone beam source 14 follows the scan path 20, the detector 16 acquires many sets of cone beam projection data, each set representative of the x-ray attenuation caused by the object O at each of a plurality of source/detector positions along the scan path 20. The cone beam projection data is then manipulated to reconstruct a 3D image of the object using any suitable image reconstruction protocol.

Figure 3:
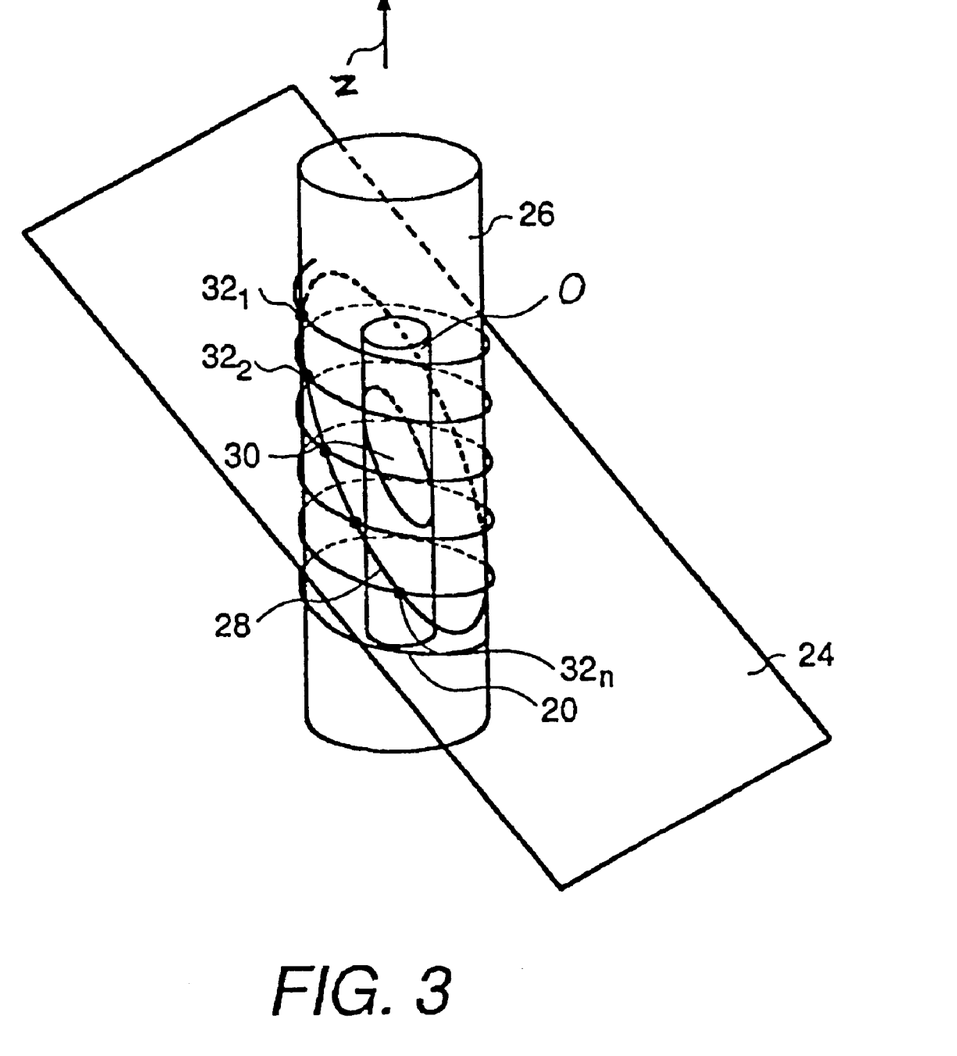
FIG. 3 is an isometric view of an exemplary planar intersection through the surface of a cylinder defined by the helical scanning trajectory, wherein such defined cylinder encloses an object in a field of view.

It is known in the art that to ensure that the cone beam data set acquired via such scanning trajectory is complete, each plane passing through the object O should cut the scanning trajectory 20 in at least one point. For example, as shown in FIG. 3, any plane (such as plane 24) intersecting the object O must also intersect the boundary of the geometric surface which surrounds object O, being that the scanning trajectory 20 is defined upon such geometric surface. In the case illustrated in FIG. 3, the geometric surface corresponds to the surface of a cylinder 26 that surrounds the object O. In the exemplary diagram, the curve of intersection between plane 24 and cylinder 26 comprises an ellipse 28. Further, it is shown that the curve of intersection between plane 24 and the cylindrical object O is also an ellipse 30 which is enclosed by scanning ellipse 28. Therefore, it should be appreciated that since the scanning helical path lies on the surface of cylinder 26, then the scan path intersects plane 24 at points $32_1$ . . . $32_n$ that collectively lie on the boundary of the geometric surface upon which the helical path is defined, that is, such points of intersection lie on scanning ellipse 28.

Referring again to FIG. 2, the criterion that any plane intersect at least one point on the scan path generally assumes that the detector 16 is fixed relative to the source 14 and that the entire object can be scanned within the field of view of the source. As explained in the above-incorporated U.S. Pat. No. 5,390,112, for example, the foregoing criterion can be advantageously satisfied if the height dimension H of the detector 16 extends just sufficiently along a direction generally parallel to axis Z to span at least the two consecutive stages in the helical path having the largest spacing therebetween as represented by L, that is, the largest spacing between corresponding points of such consecutive stages along axis Z. In some applications, the spacing between successive stages could vary depending on the specific scanning implementation. Alternatively, the scanning trajectory may be comprised of stages wherein the spacing L (i.e., pitch) between any two successive stages along axis Z is substantially equidistant.

In a cone beam CT system, to achieve optimal performance and efficiency of the detector, an optimal spiral pitch L is selected based on the detector height H. Since the pitch is determined by the table translation speed, the fixed pitch means that the table translation speed is fixed for the cone beam CT system. Thus, an optimum spiral pitch is determined by the detector height H and therefore is not adjustable.

In some circumstances, however, it is desirable to increase the photon counts on the detector to enhance the S/N for the reconstructed image. Photon counts are increased by, e.g., maintaining the scan time, and decreasing the table translation speed, which in turn reduces the spiral pitch. If the pitch is smaller, since the detector size is fixed, only a center portion of the detected cone beam image contributes to image reconstruction, and the data at the top and bottom edges of the detector amount to unnecessary exposure. In other words, when the pitch of the spiral scan is reduced from the optimal pitch based on the detector geometry, the photon efficiency of the system is compromised.

Accordingly, a system and method that would provide efficient and accurate reconstruction of an image by reducing the pitch and thereby increasing the x-ray exposure to obtain higher signal-to-noise, while using the same detector, is highly desirable.

SUMMARY OF THE INVENTION

The present invention is directed to a method for 3D image reconstruction in a spiral scan cone beam computed tomography (CT) imaging system that allows the pitch of spiral scan projection to be reduced, thereby increasing the x-ray dosage to obtain a higher S/N (signal-to-noise) ratio, while achieving efficient use of the same detector. In addition, an image reconstruction protocol according to the present invention computes a correction factor for integration planes that intersect a 1/n (n=3, 5, 7, 9, etc) reduced-pitch spiral path (which surrounds a ROI) at a number of points M, where M<n (n=1, 3, 5, 7, 9, etc.), in a 1/n reduced pitch spiral scan. Despite the reduced pitch, these M<n integration planes do not provide increased flux despite (in contrast to integration planes that intersect the object and scan path in n or greater locations). Consequently, by calculating the contribution of the projected image data from the M<n planes, and adding an appropriately computed correction factor, uniform image enhancement (e.g., higher S/N ratio) can be achieved across all integration planes by virtue of the reduced pitch and correction factor.

In one aspect of the present invention, a method for image reconstruction in a spiral scan imaging system comprises the steps of:

acquiring cone beam projection data for a 1/n reduced-pitch spiral scan of a ROI (region of interest) of an object, wherein the step of acquiring comprises applying radiation from a cone beam source towards the object from a plurality of source positions along the reduced-pitch spiral scan path that encircles the ROI, and acquiring a set of cone beam projection data on an area detector, the set of cone beam data corresponding to a respective portion of the ROI at each of said source positions;

identifying a set of integration planes that intersect the ROI and that intersect the reduced-pitch spiral scan path at M<n locations;

computing a contribution of cone beam image data for the identified set of integration planes;

computing a correction factor for the identified set of integration planes and adding the correction factor to the cone beam image data associated with the identified set of integration planes so as to increase the S/N (signal-to-noise) ratio;

reconstructing an image of the ROI using, in part, the corrected cone beam image data.

In another aspect, the step of identifying a set of integration planes comprises the step of determining a set of parallel integration planes in a direction 2, wherein 2 is within an angular range determined by a first and second curved mask boundary of a data mask that is used to acquire the cone beam projection data. Preferably, the first curved mask boundary is defined by cone beam projections of at least two spiral scan path turns above a current source position, and wherein the second curved mask boundary is defined by cone beam projections of at least two spiral scan path turns below the current source position.

In another aspect, the angular range is determined by a pair of common tangents in the direction of angles $\theta_r(\infty)$ and $\theta_r(-\infty)$, respectively, which diagonally connect the first curved mask boundary and the second curved mask boundary, wherein the angle $\theta_r(\infty)=\tan^{-1}(P/2\pi R)$ is the direction of the projection of the scan path direction, wherein P denotes a pitch of the scan path and R denotes the scanning radius.

In yet another aspect, the step of computing a contribution of cone beam image data for the identified set of integration planes comprises the step of computing image data along a plurality of lines in the cone beam data in an angular range $R=[\theta_r(-\infty)-(\pi/2), \theta_r(\infty)+(\pi/2)]$ using a filtered backprojection method.

In another aspect, the step of computing a contribution of cone beam image data for the identified set of integration planes comprises the step of computing image data along a first and second parallel line in an angular range $R=[\theta_r(-\infty)-(\pi/2), \theta_r(\infty)+(\pi/2)]$ using a Hilbert Transform, wherein the first parallel line is tangent to the first curved mask boundary and the second parallel line is tangent to the second curved mask boundary.

In yet another aspect, the correction factor comprises a multiplying the contribution of the cone beam image data associated with the identified set of integration planes by a factor that corresponds to the amount of pitch reduction.

These and other objects, features and advantages of the present invention will be described or become apparent from the following detailed description of preferred embodiments, which is to be read in connection with the accompanying drawings.

BRIEF DESCRIPTION OF DRAWINGS

FIGS. 6(*a*)–6(*e*) collectively illustrate a method for efficiently acquiring cone beam data of a reduced-pitch spiral scan path, using a fixed size detector, according to one aspect of the present invention;

DETAILED DESCRIPTION OF PREFERRED EMBODIMENTS

The present invention is directed to a method for 3D image reconstruction in a spiral scan cone beam computed tomography (CT) imaging system that allows the pitch of spiral scan projection to be reduced, thereby increasing the x-ray dosage to obtain a higher S/N (signal-to-noise) ratio, while achieving efficient use of the same detector. In addition, an image reconstruction protocol according to the present invention computes a correction factor for integration planes that intersect the reduced-pitch spiral path (which surrounds a ROI) at less than "n" points in a 1/n reduced-pitch spiral scan, where n=1, 3, 5, 7, 9, etc. As explained in detail below, these integration planes do not provide increased flux despite the reduced pitch. Consequently, by calculating the contribution of the projected image data from these integration planes, and adding an appropriately computed correction factor, uniform image enhancement (e.g., higher S/N ratio) can be achieved across all integration planes by virtue of the reduced pitch and correction factor.

Figure 4:
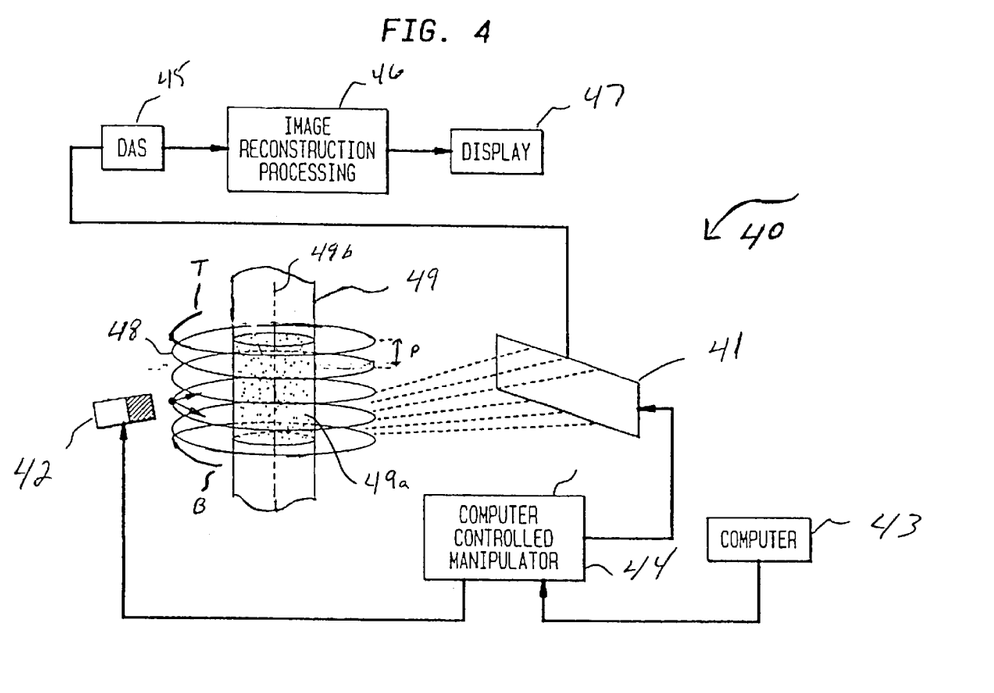
FIG. 4 illustrates a cone beam imaging system, which may be employed for performing image reconstruction according to the present invention.

FIG. 4 illustrates a spiral scan cone beam 3D CT imaging system in which an image reconstruction protocol according to the present invention may be implemented for accurately reconstructing a ROI image within an object. In a preferred embodiment, the imaging system 40 of FIG. 4 is preferably constructed and operates substantially in accordance with the principles described in, e.g., U.S. Pat. No. 5,257,183, which is incorporated herein by reference, except as to be specifically described herein with respect to implementation of an image reconstruction process according to the present invention.

Referring to FIG. 4, in response to control signals from an appropriately programmed computer 43, a computer controlled manipulator 44 causes a source 42 of a cone or pyramid shaped beam of energy (such as x-rays) and a two-dimensional pixelated detector array 41 to cooperate (scan) at a plurality of discreet, sequentially occurring, adjacent source positions along a pre-defined source scanning path. In the illustrated embodiment the scanning path is shown as a spiral scan path 48 of a ROI 49a, which is centered on a predetermined axis 49b of a long object 49. The figure assumes an upward counterclockwise rotation of the scan path 48 with a beginning portion B near the bottom of the ROI 49a and an ending portion E near the top of the ROI 49a. Further, the spiral scan path 48 is shown as being just big enough to cover the ROI 49a of the long object 49. Other types of scan paths that encircle and traverse object 49 can also be used, however, as will become apparent later, a scan path 48 exhibiting a high degree of symmetry in its parallel projection is preferred.

As a result of the source/detector cooperation under control of computer 43 and manipulator 44, at each of the source positions along path 48, x-ray energy passes through the field of view of the imaging apparatus, is attenuated by object 49a, and a set of projection data corresponding to the sensed x-ray energy falling on the elements (pixels) within detector 212 is developed. Each set of projection data is supplied to a data acquisition system (DAS) 45 which, like the previously described portions of FIG. 4, may operate in a fashion well known to those of ordinary skill in this technology for digitizing and storing of the acquired projection data. An image reconstruction model 46 implements protocols described herein for reconstruction a 3D image from the acquired projection data, which reconstructed 3D image can be displayed on display 47.

Figure 5:
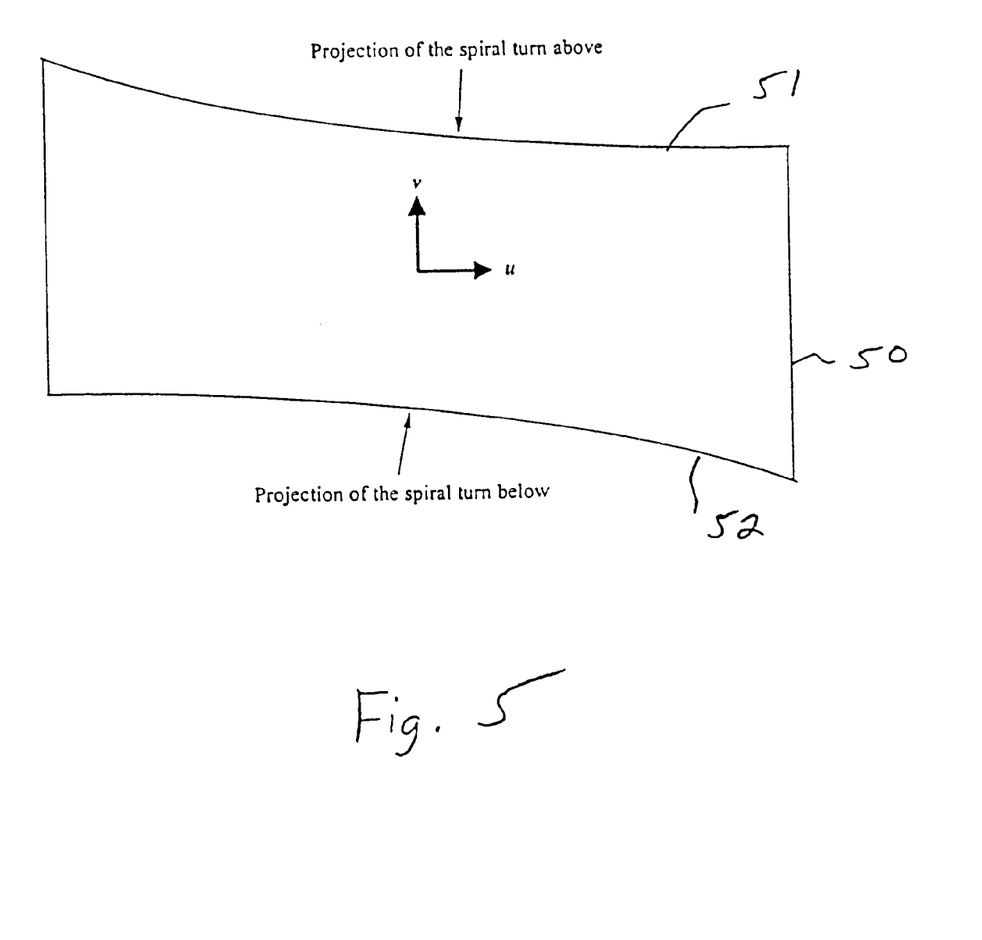
FIG. 5 illustrates a method for masking cone beam data using a spiral mask on a flat detector, which may be implemented for image reconstruction according to the present invention.

Typically, and in a preferred embodiment of the present invention, projection data for image reconstruction is acquired by applying a "mask" to each set of the projection data so that data inside the boundaries of each mask form a corresponding plurality of masked 2D data sets. One such masking method is described in U.S. Pat. No. 5,504,792 entitled METHOD AND SYSTEM FOR MASKING CONE BEAM PROJECTION DATA GENERATED FROM EITHER A REGION OF INTEREST HELICAL SCAN OR A HELICAL SCAN, issued Apr. 2, 1996, which is incorporated herein by reference. Briefly, a masking process comprises applying a spiral mask 50 (as shown in FIG. 5) to each set of projection data such that data inside the boundaries of each mask form a corresponding plurality of masked 2D data sets. The mask 50 comprises a top curve 51 and a bottom curve 52, wherein for a spiral scan path having unity pitch (i.e., pitch=1 unit), each curve is formed by cone beam projections of the spiral scan path turn above and the spiral scanpath turn below the current source position. More specifically, for a planar detector located at a rotation axis such that the line connecting a source to the origin of the detector is normal to the detector plane, the equation for the top curve 51 for the spiral scan is given by:

$$v = \frac{P}{2\pi}\tan^{-1}\left(\frac{R}{u}\right)\left(1 + \frac{u^2}{R^2}\right) \quad u \geq 0 \tag{1}$$

$$v = \frac{P}{2\pi}\left[\pi + \tan^{-1}\left(\frac{R}{u}\right)\right]\left(1 + \frac{u^2}{R^2}\right) \quad u < 0$$

where u and v are the Cartesian coordinate axes of the detector (as shown in FIG. 5) with the v axis coinciding with the rotation axis, R is the radius of the spiral, and P is the distance between adjacent spiral turns (i.e., the pitch). The bottom curve is the reflection of the top curve about the origin, i.e. (u,v)–>(–u, –v). The shape of the spiral mask 50 is shown in FIG. 5. Data in the set that is outside the mask is changed to a zero value, while data that is inside the mask is left unchanged. After a set of projection data is appropriately masked, it is referred to as a masked set of projection data, or more simply as a masked data set. Since the masks are preferably formed by cone beam projection of the spiral turn above and the turn below the current source position, the masked data set corresponds exactly to the angular range bound by the prior and the subsequent source positions, as required by the data combination principles.

In the system depicted in FIG. 4, an enhanced reconstructed image may be obtained by reducing the pitch P of the scan path 48 to increase the S/N of the image data. The pitch P of scan path 48 can be reduced by lowering the table translation speed by a factor 3, 5, 7, 9, etc., while maintaining the scan time. The increase of the S/N in the reconstructed image is attributable to, e.g., the increase in the amount of photons (image data), as well as a method according to this invention in which the data for a reduced-pitch spiral scan is acquired and processed so as to optimize the efficiency of a fixed-size detector and apply appropriate correction factors.

In accordance with one aspect of the present invention, an increase in the S/N of the image data is achieved by reducing the pitch of an original spiral scan (which pitch is optimal for the given detector size) to 1/n (where 1/n=1/3, 1/5, 1/7, etc.) of the pitch of the original spiral scan. An exemplary embodiment is described in detail herein for a 1/3 reduced-pitch scan, but the same principles are applied for other 1/n (1/5, 1/7, 1/9, etc.) reduced-pitch scans.

Figure 6:
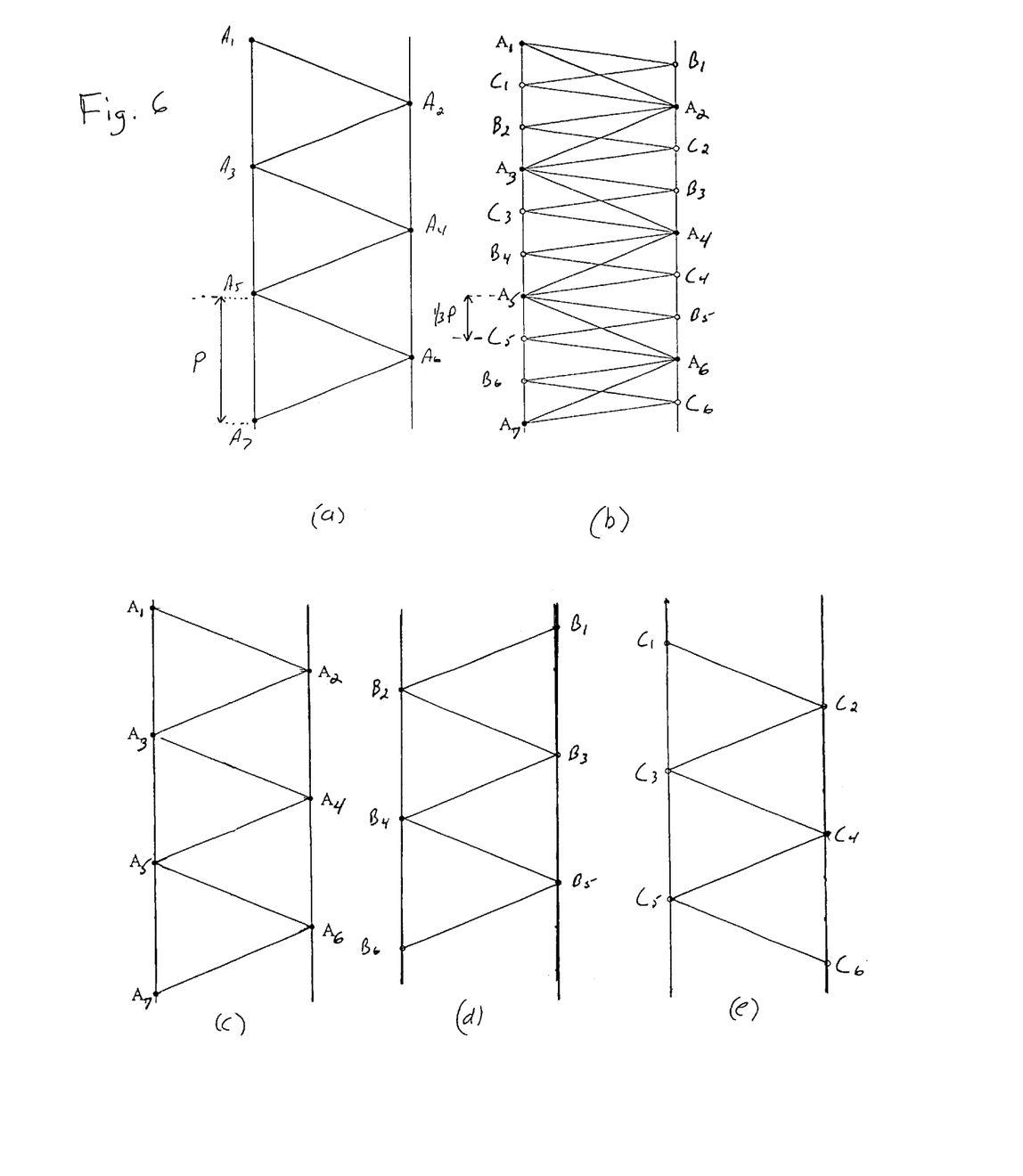

FIGS. 6(a)–6(e) are exemplary diagrams that illustrate scan path trajectories on the same integration plane for a scan path having an original pitch and a scan path having a 1/n=1/3 reduced pitch. In particular, FIG. 6a depicts, e.g., a vertical integration plane that cuts through a mid section of an object and a spiral scan path having unity pitch. The integration plane in FIG. 6s is shown to intersect a plurality of source positions $A_1$–$A_7$ that lie on the boundary of the geometric surface upon which the helical path is defined (e.g. a cylinder). The x-ray coverage of the entire integration plane is achieved by combining the coverage at each source position confined to the angular range defined by the source positions directly before and after, as shown in FIG. 6(a). For example, for source position $A_2$, the angular range of coverage is defined by source positions $A_1$ and $A_3$. One method for restricting the x-ray data to the appropriate angular range comprises a masking process as described above. Indeed, as noted above, a mask preferably comprises a top curve and a bottom curve formed by projecting the spiral turn above and the turn below from the current source position, which restricts the angular range bound by the prior and the subsequent source positions.

FIG. 6(b) depicts the spiral scan with a 1/3 reduced pitch on the same integration plane. The integration plane in FIG. 6(b) is shown to intersect a plurality of source positions $A_1$–$A_7$, $B_1$–$B_6$, and $C_1$–$C_6$, which lie on the boundary of the cylinder that defines the scan path. As shown in FIG. 6(b), a 1/3 reduction in the pitch provides a 3 times increase in the number of source positions, which substantially enhances the exposure.

Although pitch reduction increases the exposure, the efficiency of the detector in acquiring the scan projection data would decrease if, for example, in FIG. 6(b) the angular range of coverage for source position $A_2$ was limited by $C_1$ and $B_2$. Indeed, in such a case, assuming the detector height was optimized for unity pitch P, only 1/3 of the detector height (1/3 P) would be utilized for acquiring the image data.

To obtain optimal efficiency of the detector, in accordance with one aspect of the invention, assuming a pitch reduction 1/n where n=3, 5, 7, 9, . . . etc, rather than combining the data from all the source positions that the integration plane intersects, only the data from every "n" source positions are combined. This modified data combination requires a corresponding modification in the masking operation.

Figure 7:
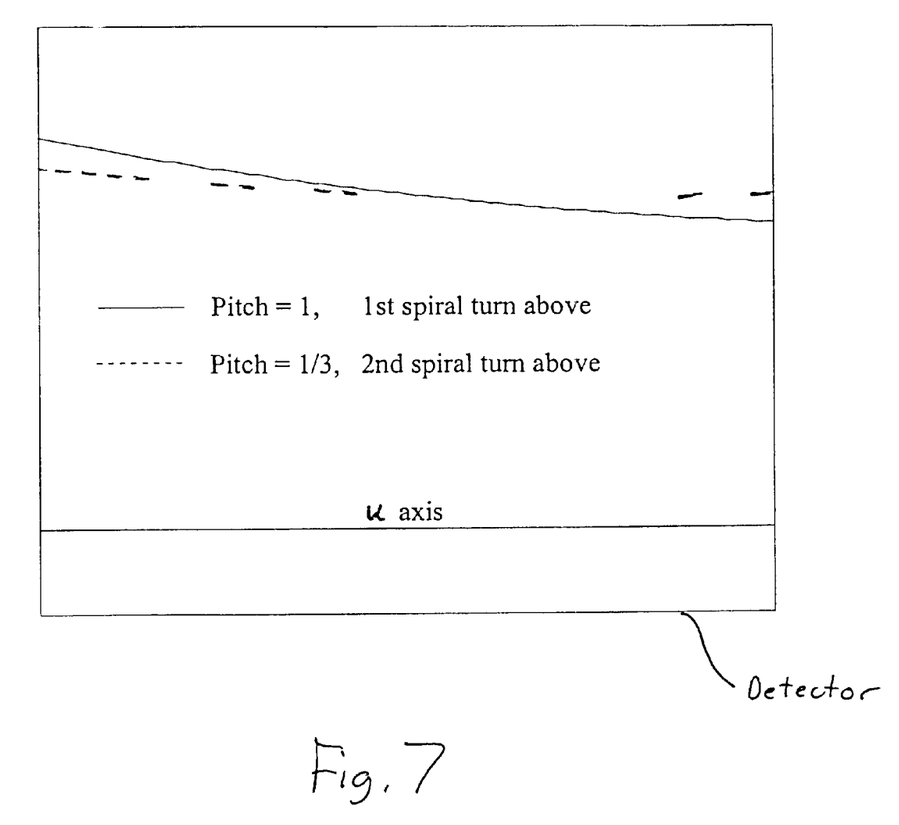
FIG. 7 is an exemplary diagram illustrating the similarity in coverage on a detector between a mask boundary of a spiral scan having unity pitch and a mask boundary of a reduced-pitch spiral scan.

For example, as illustrated in FIG. 7, a cone beam projection (dotted line) from a current source position of the second spiral turn above and the second spiral turn below for the reduced 1/3 pitch is plotted against the cone beam projection (solid line) from the current source position of the spiral turn above and the spiral turn below for the original (unity) pitch. It can be seen that the two mask boundaries are very similar in coverage. Thus, with a reduced pitch=1/3, the modified mask boundary comprises the cone beam projection from the current source position of the second spiral turn above and the second spiral turn below, thereby detecting cone beam data using essentially the entire detector area. Since there are approximately 3 times the number of source positions in the pitch=1/3 scan compared to the pitch=1 scan, the total radiation exposure in the former is thus increased approximately threefold compared to that of the latter, resulting in higher signal-to-noise ratio.

This analysis is similar in the case of 1/5 reduction in pitch wherein a modified mask boundary would comprise the cone beam projection from the current source position of the third spiral turn above and the third spiral turn below, thereby detecting cone beam data using essentially the entire detector area. Further, in the case of 1/7 reduction in pitch, a modified mask boundary would comprise the cone beam projection from the current source position of the fourth spiral turn above and the fourth spiral turn below, to thereby detect cone beam data using essentially the entire detector area.

Accordingly, an image reconstruction protocol according to one aspect of the invention will independently process "n" sets of source positions and combine the results for each set to reconstruct an image with an increased S/N. For example, the source positions of FIG. 6(b) comprise 3 sets of source positions as shown in FIGS. 6(c), 6(d) and 6(e) for source positions $A_1$–$A_7$, $B_1$–$B_6$, and $C_1$–$C_6$, respectively. More specifically, the source positions $A_1, A_2, A_3$ in FIG. 6(a) (and FIG. 6c) occupy the same locations as the source positions $A_1, A_2, A_3$ in FIG. 6(b), and thus the combination of the x-ray coverage at these source positions in FIG. 6(b) is confined to the same angular ranges as those in FIG. 6(a). Since the angular ranges at $A_1, A_2, A_3, \ldots$ in FIG. 6(b) are the same as the angular ranges at $A_1, A_2, A_3, \ldots$ in FIG. 6(a), masking process for FIG. 6(b) corresponds to the mask for the masking process for FIG. 6A.

Further, the set of source positions in FIGS. 6(d) and 6(e) each cover the integration plane via data combination for the B source positions and the C source positions in the same angular range as the A source positions so as to maximize detection efficiency.

After each set of source positions is processed using the same mask as used for pitch=1 unit (FIG. 6(a)), the net result is that the integration plane is covered 3 times. Thus, the present invention provides a mechanism by which a reduced pitch scan that increases the photon statistics, and thus the S/N, can be used while maintaining the efficient use of the fixed size detector.

In accordance with another aspect of the invention, it has been determined that the above masking/image reconstruction method works for every integration plane that intersects the ROI except for the integration planes that intersect the ROI and intersect the 1/n reduced-pitch spiral scan path at less than "n" locations. These integration planes (e.g., planes that intersect a cross-section of the object) do not provide increased coverage regardless of the decreased pitch. Assume "M" is the number of times an integration plane intersects the spiral scan path, it has been determined by the present inventor that in all instances of reduced pitch, that either M=1, or M≧3. For instance, in the exemplary embodiment described hereafter for a 1/n=1/3 reduced-pitch spiral scan, the planes that intersect the spiral scan at M=1 locations (M=1 integration planes) will not provide increased coverage by virtue of the reduced pitch. In particular, the integration planes with M≧3 will provide a corresponding increase in the cone beam data, but the integration planes with M=1 do not provide an increase (e.g., threefold in the case of 1/3 reduce pitch) in cone beam data.

As a further example, with a 1/5 reduced-pitch, the M=1, M=3 and M=4 integration planes will not provide increased coverage by virtue of the 1/5 pitch reduction, and with a 1/7 reduced pitch scan, the M=1, M=3, M=4, M=5 and M=6 integration planes do not provide increased coverage.

Figure 9:
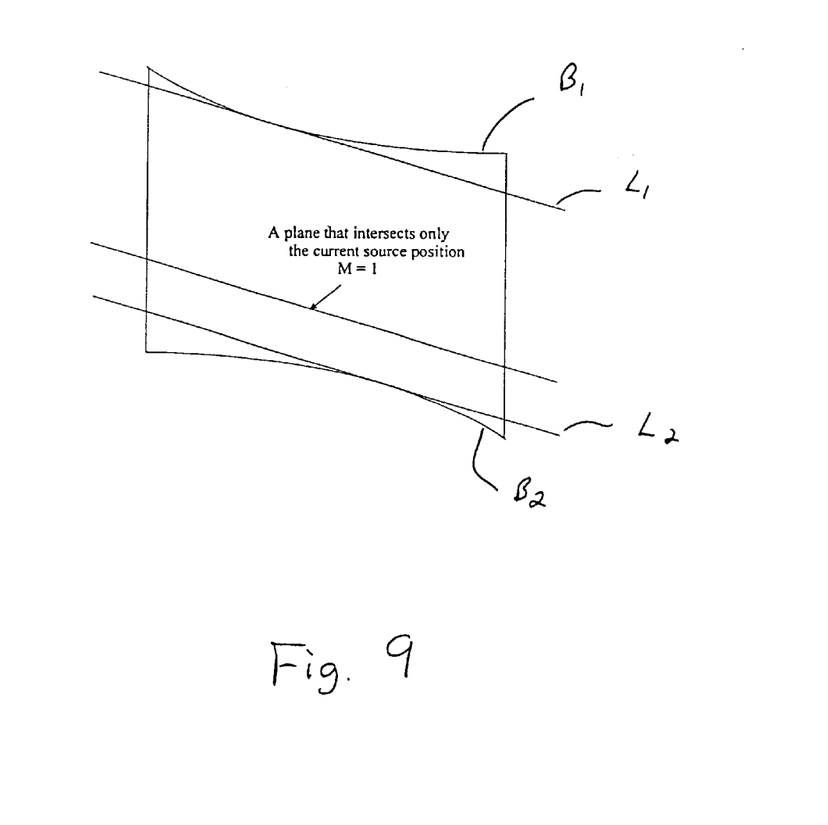
FIG. 9 is an exemplary diagram illustrating integration planes for which a correction factor is computed for an image reconstruction method according to one aspect of the present invention.

FIG. 9 is an exemplary diagram that illustrates M=1 integration planes on a data mask comprising an upper mask boundary $B_1$ and a lower mask boundary $B_2$. A line $L_1$ is tangent to $B_1$, line $L_2$ is tangent to $B_2$ and lines $L_1$ and $L_2$ are parallel. Each integration plane (such as the depicted M=1 plane) that is parallel to, and located between, lines $L_1$, $L_2$ are deemed M=1 planes because such planes do not intersect either mask boundary $B_1$, $B_2$.

Generally, in a preferred embodiment of the invention, a method for image reconstruction for a 1/n reduced-pitch spiral scan comprises the steps of identifying a sets of integration planes the intersect the spiral scan at M<n locations, computing a contribution of cone beam image data for the set of M<n integration planes, then for each set of M<n planes, adding a correction factor to the associated contribution to thereby obtain a uniform increase of the cone beam data across all integration planes. The cone beam data (comprising the correction factor) is then used to reconstruct the image. Accordingly, an accurate image with increased S/N can be obtained.

Figure 8:
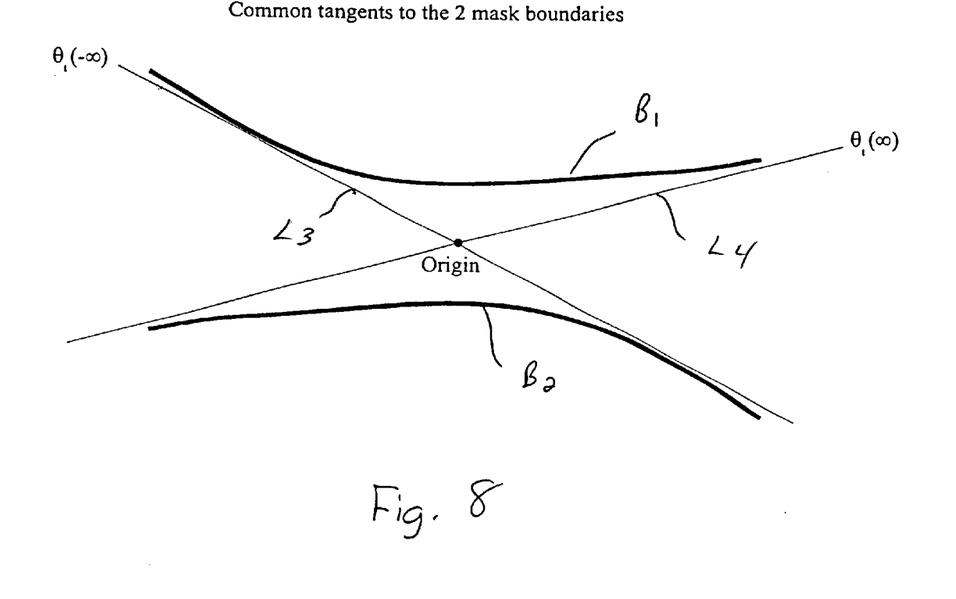
FIG. 8 is a diagram that illustrates a method according to one aspect of the present invention for identifying integration planes (M=1 planes) having a direction that intersect a reduced-pitch spiral scan at a single point, wherein an angular range in which such integration planes are found is based on a pair of common tangents to the boundaries of a data mask.

More specifically, in an exemplary embodiment described herein with a 1/3 reduced pitch, for example, the step of determining the M=1 planes comprises first determining the integration planes that are within a certain angular range based on mask boundaries of the data mask that is used to acquire the data. For example as depicted in FIG. 8, the angular range in which M=1 planes are found is based on a pair of common tangents at angles $\theta_t(\infty)$ and $\theta_t(-\infty)$ respectively connecting the upper mask boundary $B_1$ and lower mask boundary $B_2$ diagonally. In other words, L3 and L4 are common tangents to both mask boundaries. In addition, the angle $\theta_t(\infty)=\tan^{-1}(P/2\pi R)$ is the direction of the projection of the scan path direction, wherein P is the pitch of the spiral scan and R is the radius of the spiral scan. It is to be appreciated that each set of parallel integration planes in a direction $\theta$ that falls within the above angular range (as depicted in FIG. 9) will not intersect a mask boundary B1, B2 and are thus deemed M=1 planes. On the other hand, each set of parallel integration planes in a direction $\theta$ that falls outside the above angular range will intersect a mask boundary B1, B2. Accordingly, for, e.g., a 1/3 reduced-pitch, all M=1 planes are restricted within the angular range shown in FIG. 8.

Figure 1A:
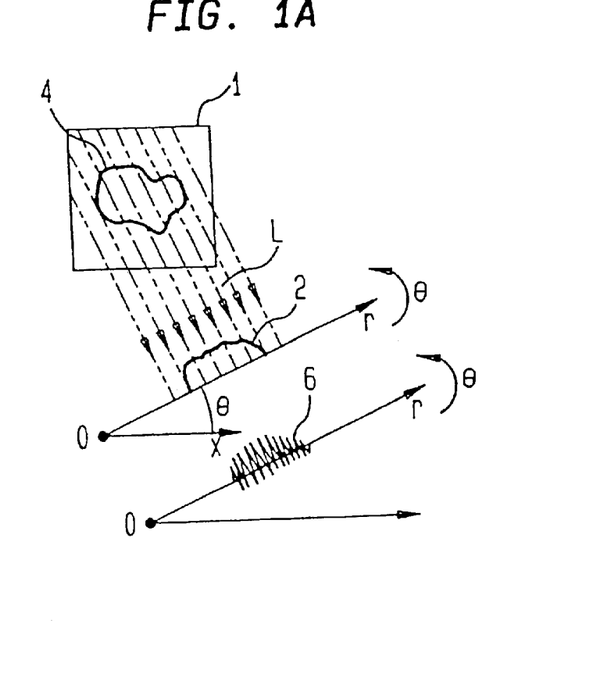
FIGS. 1A and 1B illustrate a conventional 3D backprojection method, which may be implemented with a cone beam image reconstruction method according to the present invention.

Once the relevant set of M<n integration planes are identified, a next step involves computing a contribution of cone beam image data for each set of such integration planes using any suitable procedure for processing cone beam data. For instance, in one exemplary embodiment of the present invention, the contribution of a set of M=1 planes (for a 1/3 reduced-pitch) to the cone beam image is computed using a filtered backprojection (FBP) cone beam image reconstruction technique, which is known in the art. Briefly, the FBP technique comprises the following steps at each cone beam view (i.e., at each position of the radiation source as it scans about the object, and at which an imaging detector acquires a corresponding set of projection data):

1. Compute a 1-dimensional projection (i.e., line integral) of the measured cone beam image acquired on a detector plane 1 at each of a plurality of angles 2. This step is illustrated by FIG. 1A for a given angle $2_1$ of a plurality of angles 2, where the projection 2 at coordinates (r, 2) comprises the integrated values of the cone beam image 4 on detector plane 1 along a plurality of parallel lines L(r, 2) that are normal to angle 2, each line L being at an incremental distance r from an origin O. Generally, if the detector plane 1 comprises an N by N array of pixels, then the number of angles 2 is typically given by BN/2. since, as indicated above, the angle 2 is normal to the projection line, this step is applied to the cone beam image in the limited angular range $R=[\theta_t(-\infty)-(\pi/2), \theta_t(\infty)+(\pi/2)]$, and only to the projections in the center portion of each angle 2 bound by the two lines in the direction 2 and tangential to the mask boundaries as shown in FIG. 8.

2. Filter each 1D projection in accordance with a d/dr filter, resulting in a new set of values at each of the r, 2 coordinates, such as shown by filtered projection 6 for the angle $2_1$ in FIG. 1A.

Figure 1B:
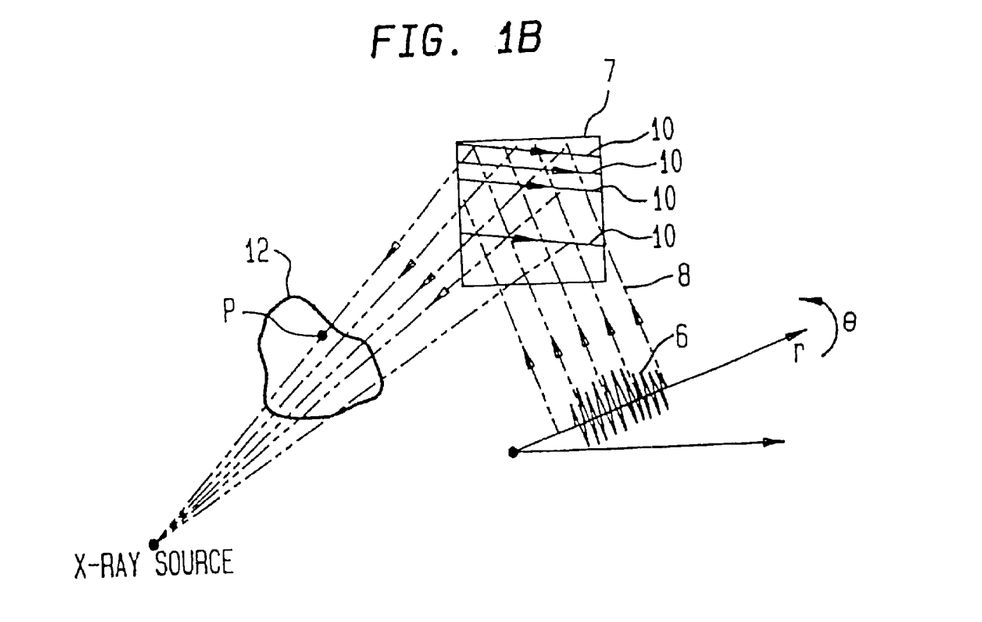

3. Backproject the filtered projection 6 from each angle 2 into a 2D object space 7 that coincides with the detector plane 1. This step is illustrated by FIG. 1B, wherein lines 8 spread the value from each r, 2 coordinate into 2D space 7 in a direction normal to each 2.

4. Perform a 1D d/dt filtering of the backprojection image formed in 2D space 7 by step 4. The 1D filtering is performed in the direction of the scan path, i.e., along lines 10, where the arrowhead points in the direction of the scan path.

5. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the spatial coordinates of the x-ray source.

In accordance with one aspect of the present invention, once the above contribution for each set of, e.g., M=1 planes is computed using steps 1–4 as above, the next step is to multiply the contribution for each set of M=1 planes by an appropriate factor based on the amount of pitch reduction. For instance, with a reduced 1/3 pitch, the contribution of the M=1 planes is multiplied by a factor of 2 to obtain a correction factor. This correction factor is then added to the original contribution to obtain corrected image data.

Once the correction factor has been applied for all sets of, e.g., M=1 planes, image reconstruction process is performed using the above weighed 3D backprojection (step 5) process. It is to be understood that in another embodiment, for a given set of M=1 planes, an enhanced image may be obtained by performing the 3D backprojection step on the original contribution of a set of M=1 planes to obtain one image, and then performing the 3D backprojection on the associated correction to obtain another image, and then adding the reconstructed images.

In another embodiment of the present invention, the step of computing the contribution of the, e.g., M=1 planes comprises computing a 1D Hilbert transform along a pair of parallel lines in a direction 2, one of which is tangential to one of the mask boundaries and the other of which is tangential to the other mask boundary. The Hilbert Transform is well known in the art and a description of such transform can be found, for example, in U.S. Pat. No. 6,292,525, issued to Kwok Tam on Sep. 18, 2001, which is incorporated by reference.

Figure 10:
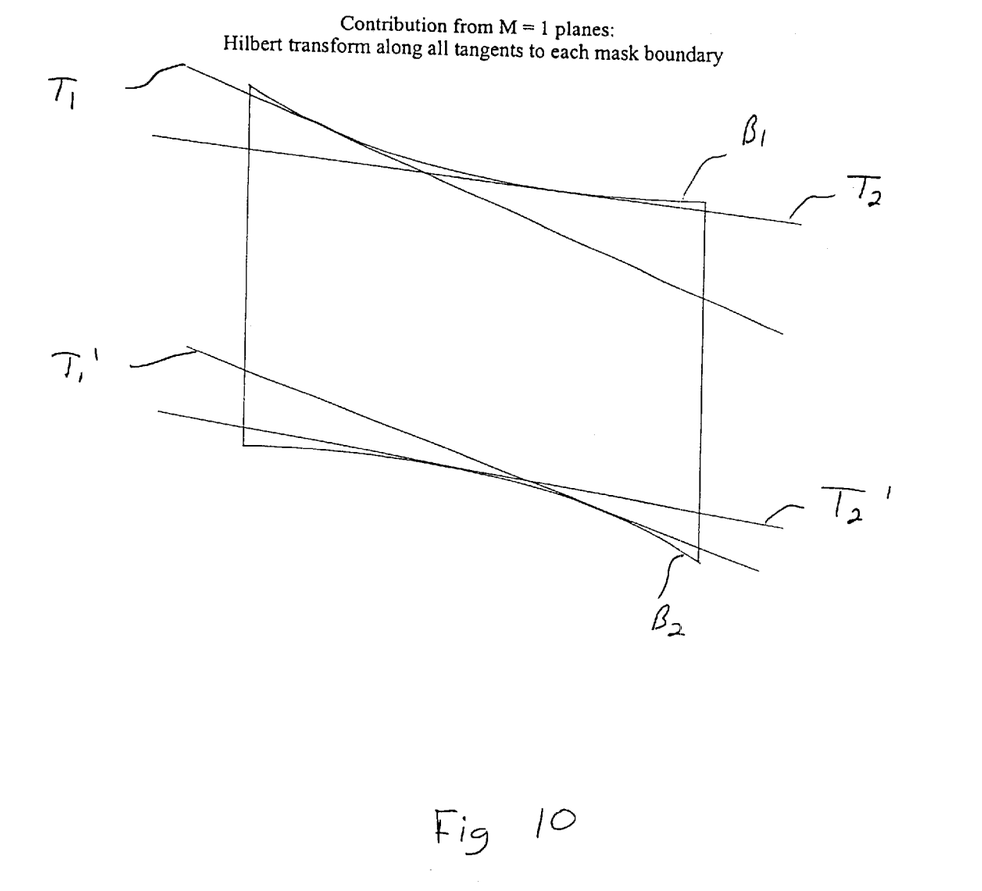
FIG. 10 is a diagram illustrating method for computing a correction factor for integration planes using a Hilbert Transform.

The use of the Hilbert Transform simplifies the computation of the contribution of the, e.g., M=1 planes. Indeed, with the FBP approach described above, for a given angle 2, the FBP computation is performed on all the parallel lines between the lines that are tangent to the boundaries. In contrast, with the Hilbert Transform, although the angular range for 2 is the same as described above, for each direction 2, only two lines need to be processed using the Hilbert transform, which simplifies the computation. For example, as shown in FIG. 10, the two parallel lines $T_1$ and $T'_1$ represent the two lines in a direction of 2 within the angular range $R=[\theta_t(-\infty)-(\pi/2), \theta_t(\infty)+(\pi/2)]$, where $T_1$ is tangent to mask boundary $B_1$ and $T_1'$ is tangent to the mask boundary $B_2$. Likewise, the two parallel lines $T_2$ and $T_2'$ represent the two lines in a direction of 2 within the angular range $R=[\theta_t(-\infty)-(\pi/2), \theta_t(\infty)+(\pi/2)]$, where $T_2$ is tangent to mask boundary $B_1$ and $T_2'$ is tangent to the mask boundary $B_2$.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for image reconstruction in a spiral scan imaging system, comprising the steps of:

acquiring cone beam projection data for a 1/n reduced-pitch spiral scan of a ROI (region of interest) of an object, wherein the step of acquiring comprises applying radiation from a cone beam source towards the object from a plurality of source positions along the 1/n reduced-pitch spiral scan path that encircles the ROI, and acquiring a set of cone beam projection data on an area detector, the set of cone beam data corresponding to a respective portion of the ROI at each of said source positions;

identifying a set of integration planes that intersect the ROI and that intersect the 1/n reduced-pitch spiral scan path at M<n locations;

computing a contribution of cone beam image data for the identified set of integration planes;

computing a correction factor for the identified set of integration planes and adding the correction factor to the cone beam image data associated with the identified set of integration planes so as to increase the S/N (signal-to-noise) ratio;

reconstructing an image of the ROI using the corrected cone beam image data.

2. The method of claim 1, wherein the step of identifying a set of integration planes comprises the step of determining a set of parallel integration planes in a direction 2, wherein 2 is within an angular range determined by a first and second curved mask boundary of a data mask that is used to acquire the cone beam projection data.

3. The method of claim 2, wherein the first curved mask boundary is defined by cone beam projections of at least two spiral scan path turns above a current source position, and wherein the second curved mask boundary is defined by cone beam projections of at least two spiral scan path turns below the current source position.

4. The method of claim 2, wherein the angular range is determined by a pair of common tangents in the direction of angles $\theta_t(\infty)$ and $\theta_t(-\infty)$, respectively, which diagonally connect the first curved mask boundary and the second curved mask boundary.

5. The method of claim 4, wherein the angle $\theta_t(\infty)=\tan^{-1}(P/2\pi R)$ is the direction of the projection of the scan path direction, wherein P denotes a pitch of the spiral scan path and R denotes a scanning radius.

6. The method of claim 4, wherein the step of computing a contribution of cone beam image data for the identified set of integration planes comprises the step of computing image data along a plurality of lines in the cone beam data in an angular range $R=[\theta_t(-\infty)-(\pi/2), \theta_t(\infty)+(\pi/2)]$ using a filtered backprojection method.

7. The method of claim 4, wherein the step of computing a contribution of cone beam image data for the identified set of integration planes comprises the step of computing image data along a first and second parallel line in an angular range $R=[\theta_t(-\infty)-(\pi/2), \theta_t(\infty)+(\pi/2)]$ using a Hilbert Transform, wherein the first parallel line is tangent to the first curved mask boundary and the second parallel line is tangent to the second curved mask boundary.

8. The method of claim 1, wherein the correction factor comprises a multiplying the contribution of the cone beam image data associated with the identified set of integration planes by a factor that corresponds to the amount of pitch reduction.

9. A program storage device readable by a machine, tangibly embodying a program of instructions executable by the machine to perform method steps for image reconstruction in a spiral scan imaging system, the method steps comprising:

acquiring cone beam projection data for a 1/n reduced-pitch spiral scan of a ROI (region of interest) of an object, wherein the step of acquiring comprises applying radiation from a cone beam source towards the object from a plurality of source positions along the reduced-pitch spiral scan path that encircles the ROI, and acquiring a set of cone beam projection data on an area detector, the set of cone beam data corresponding to a respective portion of the ROI at each of said source positions;

identifying a set of integration planes that intersect the ROI and that intersect the reduced-pitch spiral scan path at M<n locations;

computing a contribution of cone beam image data for the identified set of integration planes;

computing a correction factor for the identified set of integration planes and adding the correction factor to the cone beam image data associated with the identified set of integration planes so as to increase the S/N (signal-to-noise) ratio;

reconstructing an image of the ROI using, in part, the corrected cone beam image data.

10. The program storage device of claim 9, wherein the instructions for performing the step of identifying a set of integration planes comprise instructions for performing the step of determining a set of parallel integration planes in a direction 2, wherein 2 is within an angular range determined by a first and second curved mask boundary of a data mask that is used to acquire the cone beam projection data.

11. The program storage device of claim 10, wherein the first curved mask boundary is defined by cone beam projections of at least two spiral scan path turns above a current source position, and wherein the second curved mask boundary is defined by cone beam projections of at least two spiral scan path turns below the current source position.

12. The program storage device of claim 10, wherein the angular range is determined by a pair of common tangents in the direction of angles $\theta_t(\infty)$ and $\theta_t(-\infty)$, respectively, which diagonally connect the first curved mask boundary and the second curved mask boundary.

13. The program storage device of claim 12, wherein the angle $\theta_t(\infty)=\tan^{-1}(P/2\pi R)$ is the direction of the projection of the scan path direction, wherein P denotes a pitch of the spiral scan path and R denotes a scanning radius.

14. The program storage device of claim 12, wherein instructions for performing the step of computing a contribution of cone beam image data for the identified set of integration planes comprise instructions for performing the step of computing image data along a plurality of lines in the cone beam data in an angular range $R=[\theta_t(-\infty)-(\pi/2), \theta_t(\infty)+(\pi/2)]$ using a filtered backprojection method.

15. The program storage device of claim 12, wherein the instructions for performing the step of computing a contribution of cone beam image data for the identified set of integration planes comprise instructions for performing the step of computing image data along a first and second parallel line in an angular range $R=[\theta_t(-\infty)-(\pi/2), \theta_t(\infty)+(\pi/2)]$ using a Hilbert Transform, wherein the first parallel line is tangent to the first curved mask boundary and the second parallel line is tangent to the second curved mask boundary.

16. The program storage device of claim 9, wherein the correction factor comprises a multiplying the contribution of the cone beam image data associated with the identified set of integration planes by a factor that corresponds to the amount of pitch reduction.

* * * * *